(12) United States Patent
Clomburg, Jr. et al.

(10) Patent No.: US 8,470,059 B2
(45) Date of Patent: Jun. 25, 2013

(54) PROCESS FOR PRODUCING A METHANE-RICH GAS

(75) Inventors: Lloyd Anthony Clomburg, Jr., Houston, TX (US); Anand Nilekar, Houston, TX (US)

(73) Assignee: Shell Oil Company, Houston, TX (US)

( * ) Notice: Subject to any disclaimer, the term of this patent is extended or adjusted under 35 U.S.C. 154(b) by 537 days.

(21) Appl. No.: 12/649,171

(22) Filed: Dec. 29, 2009

(65) Prior Publication Data

US 2010/0162627 A1 Jul. 1, 2010

Related U.S. Application Data

(60) Provisional application No. 61/141,828, filed on Dec. 31, 2008.

(51) Int. Cl.
*C01B 3/24* (2006.01)
(52) U.S. Cl.
USPC .......................... 48/198.1; 48/127.1
(58) Field of Classification Search
None
See application file for complete search history.

(56) References Cited

U.S. PATENT DOCUMENTS

| | | | |
|---|---|---|---|
| 3,128,163 A | 4/1964 | Weittenhiller et al. | 48/197 |
| 3,666,682 A | 5/1972 | Muenger | 252/373 |
| 3,904,389 A | 9/1975 | Banquy | 48/215 |
| 3,928,001 A * | 12/1975 | Child et al. | 48/197 R |
| 3,970,435 A | 7/1976 | Schultz et al. | 48/61 |
| 4,017,274 A * | 4/1977 | Galstaun | 48/214 A |
| 4,134,908 A | 1/1979 | Steiner et al. | 260/449.6 M |
| 4,208,191 A | 6/1980 | Sze | 48/210 |
| 4,235,044 A | 11/1980 | Cheung | 48/197 R |
| 4,298,694 A | 11/1981 | Skov | 518/704 |
| 4,431,751 A | 2/1984 | Hohlein et al. | 518/706 |
| 4,839,391 A | 6/1989 | Range et al. | 518/712 |
| 6,755,980 B1 | 6/2004 | Van Den Born et al. | 210/767 |
| 2002/0004533 A1 | 1/2002 | Wallace et al. | 518/712 |
| 2002/0055545 A1 | 5/2002 | Sheppard et al. | 518/702 |
| 2006/0260191 A1 | 11/2006 | Van den Born et al. | 48/197 |
| 2007/0011945 A1 | 1/2007 | Grootveld et al. | 48/197 |
| 2008/0132588 A1 | 6/2008 | Pedersen et al. | 518/711 |
| 2008/0142408 A1 | 6/2008 | Eilers et al. | 208/61 |
| 2008/0172941 A1 | 7/2008 | Jancker et al. | 48/73 |

FOREIGN PATENT DOCUMENTS

| | | |
|---|---|---|
| CH | 499614 | 11/1970 |
| DE | 2624396 | 12/1976 |
| DE | 2914806 | 10/1979 |
| DE | 2949588 | 6/1980 |

(Continued)

OTHER PUBLICATIONS

"Gasification" by Christopher Higman and Maarten van der Burgt, published by Elsevier (2003), especially chapters 4 and 5.

(Continued)

*Primary Examiner* — Imran Akram

(57) ABSTRACT

A process for producing a methane-rich gas comprising the steps of:
  a) mixing a feed gas, comprising carbon monoxide and hydrogen, and a recycled methane-rich gas, comprising methane, to produce a gas mixture, comprising carbon monoxide, hydrogen and methane;
  b) reacting at least part of the carbon monoxide and hydrogen in the gas mixture in the presence of a methanation catalyst to produce a methane-rich product gas comprising methane, carbon dioxide and water;
  c) treating at least part of the methane-rich product gas to remove carbon dioxide to produce a methane-rich carbon dioxide-lean gas; and
  d) recycling at least part of the methane-rich carbon dioxide-lean gas to mixing step a) as recycled methane-rich gas.

13 Claims, 2 Drawing Sheets

FOREIGN PATENT DOCUMENTS

| | | |
|---|---|---|
| DE | 3121991 | 8/1982 |
| EP | 45352 | 7/1981 |
| EP | 0661373 | 7/1995 |
| EP | 0722999 | 7/1996 |
| EP | 1958921 | 8/2008 |
| GB | 2018818 | 10/1979 |
| WO | WO9953561 | 10/1999 |
| WO | WO0073404 | 12/2000 |
| WO | WO2007025691 | 3/2007 |
| WO | WO2007125047 | 11/2007 |

OTHER PUBLICATIONS

Xu, Jianguo et al., "Methane Steam Reforming, Methanation and Water-Gas Shift: I. Intrinsic Kinetics," AlChE Journal, Jan. 1989, vol. 35, No. 1, pp. 88-96.

Holm-Larsen, H., "$CO_2$ reforming for large scale methanol plants—an actual case," Haldor Topsoe A/S, date unknown, 6 pages.

* cited by examiner

PROCESS FOR PRODUCING A METHANE-RICH GAS

This application claims the benefit of U.S. Provisional Application No. 61/141,828 filed Dec. 31, 2008, which is incorporated herein by reference.

TECHNICAL FIELD OF THE INVENTION

The invention relates to a process for producing a methane-rich gas.

BACKGROUND OF THE INVENTION

A methanation reaction is a catalytic reaction of hydrogen with carbon monoxide and/or carbon dioxide to produce a methane-rich gas. This methane-rich gas is sometimes also referred to as synthetic natural gas (SNG) and can be used as substitute gas for natural gas. In areas where there is little natural gas available, other sources of energy, such as coal or petroleum coke, may be partially oxidized in a gasification process to produce a gas comprising hydrogen and carbon monoxide. Such a gas comprising hydrogen and carbon monoxide is sometimes also referred to as synthesis gas. The synthesis gas can subsequently be used to produce synthetic natural gas (SNG) in a methanation process.

The methanation reaction proceeds, in the presence of a suitable methanation catalyst, in accordance with the following equations:

$$CO + 3H_2 = CH_4 + H_2O + \text{heat} \qquad (1)$$

$$CO_2 + 4H_2 = CH_4 + 2H_2O + \text{heat} \qquad (2).$$

The water formed during the reaction can, depending on the catalyst, temperature and concentrations present, subsequently react in-situ with carbon monoxide present in a water-gas shift reaction in accordance with the following equation:

$$CO + H_2O = CO_2 + H_2 + \text{heat} \qquad (3)$$

Reaction (1) is considered the main reaction and reactions (2) and (3) are considered to be side reactions. All the reactions are exothermic.

The methanation reaction can be carried out in one or more adiabatic reactors. As only a partial conversion may be achieved in one adiabatic reactor, conventionally a series of adiabatic reactors is used in a methanation process. As the methanation reaction is exothermic, the temperature of a reaction mixture will increase during passage through the adiabatic reactors. The methanation reactions are reversible and an increasing temperature will tend to shift the equilibrium towards a lower yield. When a series of adiabatic reactors is used, the effluent of an adiabatic reactor is therefore cooled before entering a subsequent adiabatic reactor, for example by using external heat exchangers. In addition, the temperature increase in a first adiabatic reactor is conventionally limited by diluting a feed gas entering the first adiabatic reactor with a methane-rich gas. For this purpose a considerable portion of methane-rich product gas generated in the first adiabatic reactor is cooled and recycled. For example, a feed gas to a first adiabatic reactor may be mixed with recycled methane-rich gas in a volume ratio of recycled methane-rich gas to feed gas as high as about 6:1.

Due to this large recycle stream, a large volume of gas needs to be processed through the first adiabatic reactor. As a consequence such a first adiabatic reactor conventionally has a large volume that may be as high as about 600 or 700 cubic meters. In addition the compressor load for any compressor used to compress the recycled methane-rich gas is high.

An example of a conventional methanation process is provided in the report titled "Haldor Topsøe's Recycle Energy-efficient methanation process" which is available from the website of Haldor Topsøe, www.topsoe.com. In the methanation process illustrated on page 4 of the report a feed comprising hydrogen and carbon monoxide is fed to a series of three adiabatic reactors. After each adiabatic reactor the reactor effluent is cooled in a heat exchanger and part of the reactor effluent of the first adiabatic reactor is cooled, recycled and mixed with the feed gas.

GB2018818 describes a process for preparing a methane-rich gas in at least one adiabatically operating methanation reactor by converting a combination of a preheated synthesis gas stream and a recycle stream from the methanation reactor. The combined preheated synthesis gas stream and recycle stream are passed through a layer of shift catalyst directly before passage through a methanation catalyst. The process of GB2018818 is illustrated with three experiments. GB2018818 states that because of the limitations of the used compressor and in contradistinction with the intended industrial operation the outlet stream of the reactor in these experiments was cooled to below 100° C. According to GB2018818, hereby all the steam was condensed out, whereafter the dry outlet stream was divided into a recycle stream and a product stream. After compression of the recycle stream and before feeding of the recycle stream into the reactor a calculated amount of water was added to the recycle stream to compensate for the removed water. The volumetric ratio of the recycle stream to the synthesis gas stream in the experiments was in the range of 2:1 to 3:1. The volumetric ratio of the recycle stream to the product stream was in the range from 4:1 to 5:1.

U.S. Pat. No. 4,235,044 describes a process for the methanation of a synthesis gas wherein a synthesis gas stream is divided into two separate processing streams. A first stream is reacted with steam in a water gas shift zone to produce a converted gas stream containing carbon dioxide and hydrogen. A first portion of the second unconverted stream is added to the converted gas stream to prepare an adjusted gas stream that is adiabatically reacted in a first adiabatic reaction zone to form an effluent gas stream containing methane. The effluent gas stream from the first adiabatic reaction zone is cooled and mixed with the remaining portion of the second unconverted stream to prepare a reaction mixture that is passed to an isothermal methanation zone or to a second adiabatic methanation zone and subsequently to an isothermal methanation zone. Carbon dioxide can be removed from the product methane-rich gas or from the methanation feed gas. The process uses no recycle. In between methanation zones no carbon dioxide is removed.

U.S. Pat. No. 3,904,389 describes a process for the production of a methane-rich gas from a gaseous effluent of a fossil fuel gasification wherein the gaseous effluent is divided into two fractions. The first effluent fraction is subjected to methanation. The second effluent fraction is successively subjected to shift conversion and CO2 removal. Hereafter the resulting effluents are mixed again and subjected to another methanation. The process uses no recycle. In between methanation zones no carbon dioxide is removed.

It would be an advancement in the art to provide a methanation process that allows an adiabatic reactor to be sufficiently cooled with a small recycle stream and/or at a low ratio of recycled methane-rich gas to feed gas.

SUMMARY OF THE INVENTION

The above has been achieved with the process according to the invention.

Accordingly, the present invention provides a process for producing a methane-rich gas comprising the steps of:

a) mixing a feed gas, comprising carbon monoxide and hydrogen, and a recycled methane-rich gas, comprising methane, to produce a gas mixture, comprising carbon monoxide, hydrogen and methane;

b) reacting at least part of the carbon monoxide and hydrogen in the gas mixture in the presence of a methanation catalyst to produce a methane-rich product gas comprising methane, carbon dioxide and water;

c) treating at least part of the methane-rich product gas to remove carbon dioxide to produce a methane-rich carbon dioxide-lean gas; and d) recycling at least part of the methane-rich carbon dioxide-lean gas to mixing step a) as recycled methane-rich gas.

By removing carbon dioxide from the methane-rich product gas that is to be recycled, the volume of the recycle stream is reduced. The remaining composition of the recycle stream, however, still allows an adiabatic reactor to be sufficiently cooled with the smaller recycle stream. The ratio of recycled methane-rich gas to feed gas may even be below 2:1. In addition the reactor volume of one or more of the methanation reactors can be reduced and/or the load on one or more compressors can be reduced.

DETAILED DESCRIPTION OF THE INVENTION

Figure 1:
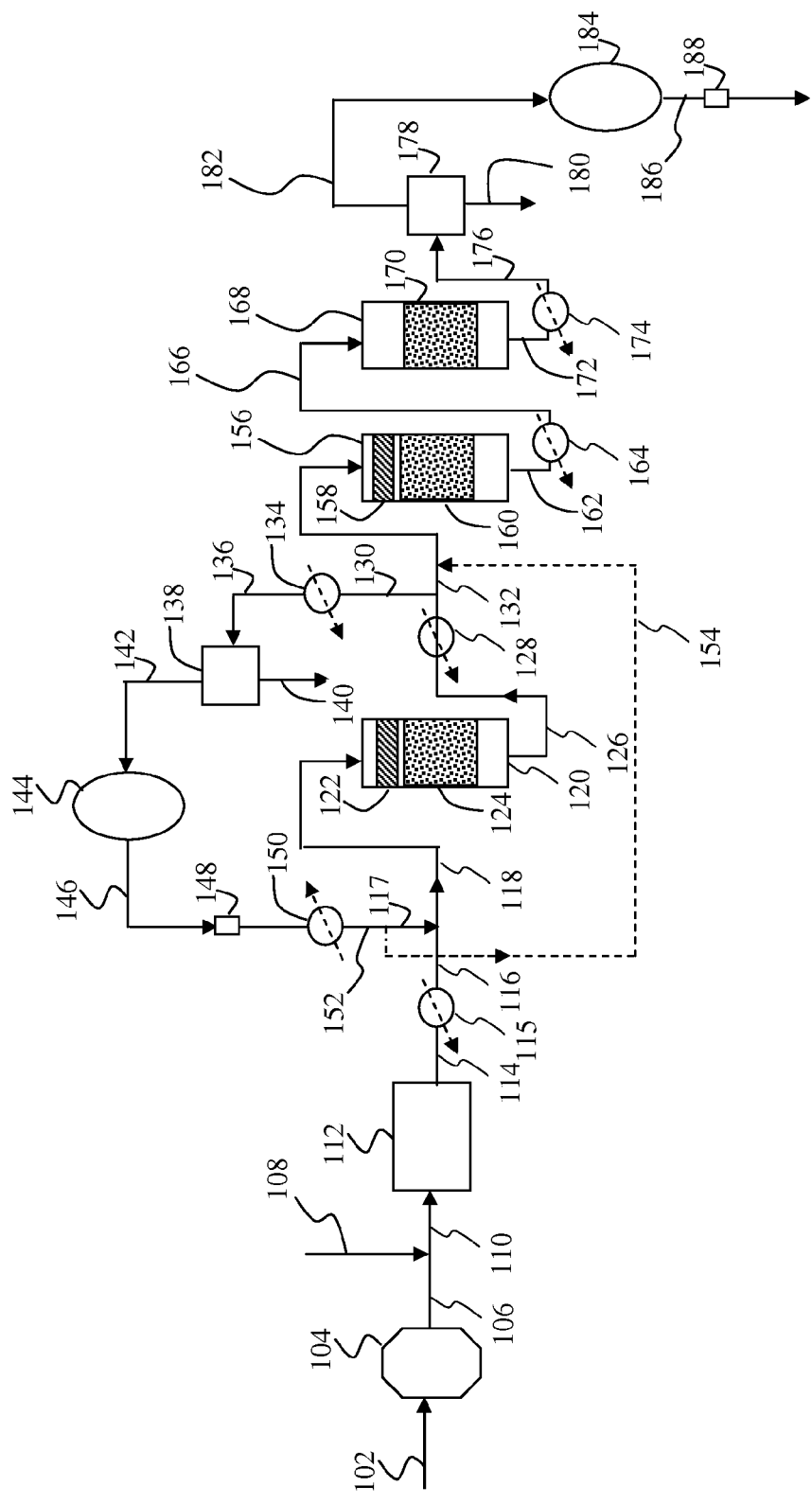
FIG. 1 schematically shows the flow scheme for an embodiment of the process according to the invention.

The feed gas in step a), comprising carbon monoxide and hydrogen, may be any gas comprising carbon monoxide and hydrogen. An example of a gas comprising carbon monoxide and hydrogen is synthesis gas. Within this patent application synthesis gas is understood to be a gas comprising at least hydrogen and carbon monoxide. In addition, the synthesis gas may comprise other compounds such as carbon dioxide, water, nitrogen, argon and/or or sulphur containing compounds. Examples of sulphur containing compounds that may be present in synthesis gas include hydrogen sulphide and carbonyl sulphide.

The synthesis gas may be obtained by reacting a carbonaceous feed and an oxidant in a gasification reaction.

By a carbonaceous feed is understood a feed comprising carbon in some form. The carbonaceous feed may be any carbonaceous feed known by the skilled person to be suitable for the generation of synthesis gas. The carbonaceous feed may comprise solids, liquids and/or gases. Examples include coal, such as lignite (brown coal), bituminous coal, sub-bituminous coal, anthracite, bitumen, oil shale, oil sands, heavy oils, peat, biomass, petroleum refining residues, such as petroleum coke, asphalt, vacuum residue, or combinations thereof. As the synthesis gas is used in a methanation process the synthesis gas is preferably obtained by gasification of a solid or liquid carbonaceous feed. In an advantageous embodiment, the synthesis gas is obtained by gasification of a solid carbonaceous feed that comprises coal or petroleum coke.

By an oxidant is understood a compound capable of oxidizing another compound. The oxidant may be any compound known by the skilled person to be capable of oxidizing a carbonaceous feed. The oxidant may for example comprise oxygen, air, oxygen-enriched air, carbon dioxide (in a reaction to generate carbon monoxide) or mixtures thereof. If an oxygen-containing gas is used as oxidant, the oxygen-containing gas used may be pure oxygen, mixtures of oxygen and steam, mixtures of oxygen and carbon dioxide, mixtures of oxygen and air or mixtures of pure oxygen, air and steam.

In a special embodiment the oxidant is an oxygen-containing gas containing more than 80 vol %, more than 85 vol %, more than 90 vol %, more than 95 vol % or more than 99 vol % oxygen. Substantially pure oxygen is preferred. Such substantially pure oxygen may for example be prepared by an air separation unit (ASU).

In some gasification processes, a temperature moderator may also be introduced into the reactor. Suitable moderators include steam and carbon dioxide.

The synthesis gas may be generated by reacting the carbonaceous feed with the oxidant according to any method known in the art. For example it may be generated by a gasification reaction in a gasification process or by a reforming reaction in a steam reforming process.

In a preferred embodiment the synthesis gas is generated by a partial oxidation of a carbonaceous feed such as coal or petroleum coke with an oxygen-containing gas in a gasification reactor.

Synthesis gas leaving a gasification reactor is sometimes also referred to as raw synthesis gas. This raw synthesis gas may be cooled and cleaned in a number of downstream cooling and cleaning steps. The total of the gasification reactor and the cooling and cleaning steps is sometimes also referred to as gasification unit.

Examples of suitable gasification processes, reactors for such gasification processes and gasification units are described in "Gasification" by Christopher Higman and Maarten van der Burgt, published by Elsevier (2003), especially chapters 4 and 5 respectively. Further examples of suitable gasification processes, reactors and units are described in US2006/0260191, WO2007125047, US20080172941, EP0722999, EP0661373, US20080142408, US20070011945, US20060260191 and U.S. Pat. No. 6,755,980.

The synthesis gas produced by reacting a carbonaceous feed and an oxidant in a gasification process may be cooled and cleaned before using it as a feed gas in step a). Synthesis gas leaving a gasification reactor can for example be cooled by direct quenching with water or steam, direct quenching with recycled synthesis gas, heat exchangers or a combination of such cooling steps, to produce a cooled synthesis gas. In the heat exchangers, heat may be recovered. This heat may be used to generate steam or superheated steam. Slag and/or other molten solids that may be present in the produced synthesis gas can suitably be discharged from the lower end of a gasification reactor. Cooled synthesis gas can be subjected to a dry solids removal, such as a cyclone or a high-pressure high-temperature ceramic filter, and/or a wet scrubbing process, to produce a cleaned synthesis gas.

In a preferred embodiment, the feed gas used in step a) has been desulphurized before mixing it with the recycled methane-rich gas. The preferably cooled and cleaned synthesis gas may thus be desulphurized to produce a desulphurized synthesis gas before it is used as feed gas. The desulphurization may be carried out in a desulphurizing unit where sulphur containing compounds such as hydrogen sulphide and carbonyl sulphide can be removed from the gas. Desulphurization can for example be carried out by so-called physical absorption and/or by a chemical solvent extraction process.

The synthesis gas may further be treated to reduce the carbon dioxide content of the synthesis gas.

In one advantageous embodiment the amount of sulphur containing compounds and the amount of carbon dioxide in the feed gas or synthesis gas has been reduced in a combined sulphur/carbon dioxide removal unit before mixing it with the recycled methane-rich gas.

In another advantageous embodiment, only part or no carbon dioxide is removed from the feed gas or synthesis gas before mixing it with the recycled methane-rich gas, thereby saving hardware costs. In this case most or all the carbon dioxide present in the synthesis gas can be removed from the methane-rich gas produced in the process.

The feed gas, which feed gas comprises carbon monoxide and hydrogen, is mixed with a recycled methane-rich gas, which recycled methane-rich gas comprises methane, to produce a gas mixture.

By a methane-rich gas is understood a gas in which the methane content has been increased. A methane-rich gas is preferably a gas comprising more than 1 molar percent methane, more preferably a gas comprising more than 5 molar percent methane and most preferably a gas comprising more than 10 molar percent methane.

By a recycled methane-rich gas is understood a methane-rich gas comprising methane that is being recycled. For example methane may be recycled to the methanation reactor in which such methane was produced.

In the process according to the invention the mixing may be achieved by simply combining a stream comprising feed gas and a stream comprising recycled methane-rich gas.

The gas mixture in step a) preferably comprises carbon monoxide and hydrogen in a molar ratio of hydrogen to carbon monoxide in the range from 0.5:1 to 20:1, preferably in the range from 1:1 to 10:1 and more preferably in the range from 1:1 to 6:1.

In one preferred embodiment the gas mixture comprises carbon monoxide and hydrogen in a molar ratio of hydrogen to carbon monoxide of about 3:1.

In one preferred embodiment the molar ratio of hydrogen to carbon monoxide in the gas mixture is increased by treating at least part of the feed gas in a water-gas shift unit before mixing it with the recycled methane-rich gas. Preferably the water-gas shift unit used to treat at least part of the feed gas comprises a high temperature water-gas shift, having a preferred feed temperature in the range from 280° C. to 340° C. Preferably essentially all feed gas is treated in a water gas shift unit before mixing it with the recycled methane-rich gas.

In the water-gas shift unit part of the carbon monoxide present in the feed gas can react with water and/or steam over a water-gas shift catalyst in a water-gas shift reaction. The water and/or steam used for the water-gas shift reaction may be water and/or steam already present in the feed gas; water and/or steam added just before or during the water-gas shift reaction; or a combination of both.

In another preferred embodiment the molar ratio of hydrogen to carbon monoxide in the gas mixture is increased by treating at least part of the gas mixture itself in a water-gas shift unit before reacting at least part of the carbon monoxide and hydrogen in the gas mixture in the presence of a methanation catalyst. Preferably the water-gas shift unit used to treat the gas mixture comprises a low temperature water-gas shift, having a preferred feed temperature in the range from 250 to 320° C. In the water-gas shift unit part of the carbon monoxide present in the gas mixture can react with water and/or steam over a water-gas shift catalyst in a water-gas shift reaction. The water and/or steam used for the water-gas shift reaction may be water and/or steam already present in the gas mixture; water and/or steam added just before or during the water-gas shift reaction; or a combination of both. Preferably the water-gas shift reaction is an in-situ water-gas shift reaction of carbon monoxide present in the gas mixture with water and/or steam already present in the gas mixture.

The water-gas shift unit can include a separate water-gas shift reactor comprising water-gas shift catalyst or can consist merely of a separate layer of water-gas shift catalyst located upstream of a methanation catalyst in a methanation reactor, such as illustrated in GB2018818.

In a preferred embodiment the molar ratio of hydrogen to carbon monoxide in the gas mixture is increased by first treating at least part of the feed gas in a water-gas shift unit, preferably comprising a separate water-gas shift reactor, to produce a shifted feed gas; then mixing the shifted feed gas with recycled methane-rich gas to produce a gas mixture; and subsequently treating at least part of the gas mixture in a water-gas shift unit, consisting merely of a separate layer of water-gas shift catalyst located upstream of a methanation catalyst in a methanation reactor.

The water-gas shift catalyst may be any catalyst known to be suitable for such purpose. The water-gas shift catalyst may for example contain copper, zinc and/or chromium, optionally in the form of oxides and/or supported by a carrier.

The, preferably shifted, feed gas is mixed with recycled methane-rich gas to produce a gas mixture, which gas mixture will comprise at least carbon monoxide, hydrogen and methane. In addition, the gas mixture may comprise other compounds such as water, carbon dioxide, nitrogen and argon.

In a preferred embodiment the molar ratio of feed gas to recycled methane-rich gas in the gas mixture is equal to or less than 2:1, more preferably equal to or less than 1:1 or most preferably equal to or less than 0.5:1. In a further practical embodiment the molar ratio of feed gas to recycled methane-rich gas in the gas mixture is equal to or more than 0.01:1.

At least part of the carbon monoxide and the hydrogen in the gas mixture are reacted in the presence of a methanation catalyst to produce a methane-rich product gas comprising at least methane, carbon dioxide and water. In addition the methane-rich product gas may comprise other compounds such as unreacted carbon monoxide, unreacted hydrogen, nitrogen and argon.

The reaction of carbon monoxide and hydrogen in the presence of the methanation catalyst may suitably be carried out in a methanation reactor. Preferably the methanation reactor is an adiabatic methanation reactor.

Within this patent application an adiabatic methanation reactor is understood to be a methanation reactor, which is not deliberately cooled or heated. In a preferred embodiment the adiabatic methanation reactor is a methanation reactor wherein there is substantially no loss or gain of heat with the surroundings of the reactor.

The methanation reactor may be vertically oriented or horizontally oriented. Preferably the methanation reactor is vertically oriented. In such a vertically oriented methanation reactor the flow of the gas mixture in the methanation reactor may be bottom-up or top-down. Preferably the flow of the gas mixture is top-down.

By using the process according to the invention the reactor volume of the methanation reactor may conveniently be reduced. The process according to the invention causes a reduction in recycle volumes leading to less volume that is to be processed through the reactors.

Preferably the methanation reactor is part of a series of methanation reactors. More preferably the methanation reactor is the first in a series of methanation reactors.

Preferably the gas mixture is fed into a methanation reactor at a temperature in the range from 250° C. to 500° C., preferably in the range from 260° C. to 400° C., and more preferably in the range from 200 to 300° C. and a pressure in the range from 10 to 60 bar, preferably in the range from 20 to 50 bar, more preferably in the range from 25 to 45 bar. The flowrate of the gas mixture into the adiabatic methanation reactor, on the basis of a plant producing 14.1 million standard cubic meters of methane-rich product gas per day, is preferably equal to or less than 150 Kmol/sec and preferably at least 10 Kmol/sec.

The methanation reactor may comprise one or more methanation catalysts and optionally one or more water-gas shift catalysts, as described herein above.

The methanation catalyst may be any methanation catalyst known to be suitable for this purpose. The methanation catalyst may comprise nickel, cobalt, ruthenium or any combination thereof. Preferably the methanation catalyst comprises nickel. The methanation catalyst may comprise nickel, cobalt or ruthenium on a carrier, which carrier may comprise for example alumina, silica, magnesium, zirconia or mixtures thereof. Preferably the catalyst is a nickel containing catalyst, comprising preferably in the range from 10 wt % to 60 wt % nickel and more preferably in the range from 10 wt % to 30 wt % nickel. The nickel containing catalyst may further comprise some molybdenum as promotor.

Examples of suitable methanation catalysts include the catalysts exemplified in GB2018818 and Haldor Topsoe's MCR-2X methanation catalyst.

The methanation catalyst(s) and/or water-gas shift catalyst(s) may be present in the methanation reactor in any form known to be suitable for catalyzing the methanation reaction respectively water-gas shift reaction. The catalyst(s) may be present as a fixed bed, coated on granules packed in a reactor or coated on for example a tubular or spiral structure within the reactor. Preferably the methanation catalyst is present as a fixed bed of catalyst. Preferably the water-gas shift catalyst is present as a fixed bed of water-gas shift catalyst upstream of a fixed bed of methanation catalyst, such that the gas mixture first passes the water-gas shift catalyst before coming into contact with the methanation catalyst. In a preferred embodiment, where the methanation reactor is a vertical reactor having a top-down flow, a layer of water-gas shift catalyst may simply be deposited onto a lower located layer of methanation catalyst. Without wishing to be bound by any kind of theory, it is believed that the water-gas shift catalyst advantageously allows water and carbon monoxide in the gas mixture to react thereby generating heat, which allows the gas mixture to increase quickly in temperature to a temperature high enough for the methanation reaction to initiate. For example, such a water-gas shift reaction may quickly increase the temperature of the gas mixture to a temperature above 300° C. but below 400° C.

At least part of the methane-rich product gas is treated to remove carbon dioxide to produce a methane-rich carbon dioxide-lean gas. By a carbon dioxide-lean gas is understood a gas from which at least part of the carbon dioxide has been removed. Preferably at least 30 molar percent, more preferably at least 50 molar percent, still more preferably at least 80 molar percent and most preferably at least 90 molar percent of the carbon dioxide is removed from the gas. In an especially preferred embodiment essentially all of the carbon dioxide is removed from the gas.

Carbon dioxide may be removed by any method known to be suitable for that purpose. For example carbon dioxide may be removed by cryogenic cooling, or by physical absorption or in a chemical solvent extraction process.

Subsequently at least part of the methane-rich carbon dioxide-lean gas can be recycled as recycled methane-rich gas to step a) for mixing with the feed gas.

In a preferred embodiment, only part of the methane-rich product gas, for example in the range from 1 to 99 molar percent, preferably in the range from 10 to 90 molar percent, more preferably in the range from 25 to 75 molar percent, most preferably in the range from 30 to 60 molar percent of the methane-rich product gas produced in step b) is treated to remove carbon dioxide.

Preferably the methane-rich product gas is split into a first part and a second part. The first part may be treated to remove carbon dioxide to produce a methane-rich, carbon dioxide-lean gas. The second part of the methane-rich product gas may be forwarded to a subsequent methanation reactor, preferable a subsequent adiabatic methanation reactor, or may be used as end product.

In a further embodiment, only part of the methane-rich carbon dioxide-lean gas is recycled to mixing step a) as recycled methane-rich gas, for example in the range from 1 to 99 molar percent, preferably in the range from 10 to 90 molar percent, more preferably in the range from 25 to 75 molar percent, most preferably in the range from 30 to 60 molar percent of the methane-rich carbon dioxide-lean gas produced in step c) is recycled to step a).

In this embodiment the methane-rich carbon dioxide-lean gas is preferably split into a first part and a second part. The first part may be recycled to step a). The second part may be mixed with the methane-rich product gas of step b) and forwarded to a subsequent methanation reactor, preferably a subsequent adiabatic methanation reactor, or may be used as end product.

In a still further embodiment, from 99 to 100 molar percent, and preferably essentially all, of the methane-rich carbon dioxide-lean gas is recycled to mixing step a) as recycled methane-rich gas.

Preferably the methane-rich product gas produced in step b) is cooled before removing the carbon dioxide to produce a cooled methane-rich product gas. Such cooling may be carried out in any manner known in the art. Preferably the methane-rich product gas is cooled in one or more heat exchanger(s). In a preferred embodiment the heat obtained from the methane-rich product gas is used to preheat water, convert water to steam and/or superheat steam in one or more of the heat exchanger(s).

In a further preferred embodiment water is removed from the methane-rich product gas, either before or after carbon dioxide has been removed, to produce a dried methane-rich gas. More preferably the methane-rich product gas produced in step b) is first cooled to produce a cooled methane-rich product gas and subsequently water is removed from the cooled methane-rich product gas to produce a dried and cooled methane-rich product gas. The dried and cooled methane-rich product gas may subsequently be treated to remove carbon dioxide to produce a methane-rich carbon dioxide-lean gas, which can be recycled to step a).

Water may be removed in any manner known in the art to be suitable for such a purpose. Preferably the water is removed in one or more flashdrum(s).

Preferably the methane-rich carbon dioxide-lean gas that is mixed as recycled methane-rich gas with the feed gas in step a) comprises less than 10 volume percent water, more preferably less than 5 volume percent water and most preferably less than 1 volume percent water; less than 10 volume percent carbon dioxide, more preferably less than 7.5 volume percent carbon dioxide and most preferably less than 5 volume percent carbon dioxide; and/or more than 25 volume percent methane, more preferably more than 30 volume percent methane. More preferably this methane-rich carbon dioxide-lean gas comprises more than 45 volume percent methane and/or more than 30 volume percent hydrogen.

In one embodiment part of the methane-rich product gas and/or part of the methane-rich carbon dioxide-lean gas may be used as end-product. Preferably, however at least part of the methane-rich product gas and/or at least part of the methane-rich carbon dioxide-lean gas is forwarded to one or more subsequent methanation reactor(s). The subsequent methanation reactor(s) may for example be multitubular reactor(s) or adiabatic reactor(s). Preferably part of the methane-rich product gas and/or part of the methane-rich carbon dioxide-lean gas is forwarded to one or two subsequent adiabatic reactors connected in series.

The process according to the invention is especially advantageous when converting a carbonaceous feed into a synthetic natural gas.

Accordingly, the present invention also provides a process for producing a methane-rich gas from a carbonaceous feed comprising the steps of a) reacting a carbonaceous feed and an oxidant in a gasification process to produce a synthesis gas comprising carbon monoxide and hydrogen; which synthesis gas is desulphurized to produce a desulphurized synthesis gas; and of which desulphurized synthesis gas at least part is reacted with water and/or steam in a water-gas shift reaction to produce a shifted synthesis gas;

which shifted synthesis gas is mixed with a recycled methane-rich gas, comprising methane, to produce a gas mixture, which gas mixture comprises carbon monoxide, hydrogen and methane;

b) reacting at least part of the carbon monoxide and hydrogen in the gas mixture in the presence of a methanation catalyst to produce a methane-rich product gas comprising methane, carbon dioxide and water;

c) treating at least part of the methane-rich product gas to remove carbon dioxide to produce a methane-rich carbon dioxide-lean gas; and d) recycling at least part of the methane-rich carbon dioxide-lean gas to step a) as recycled methane-rich gas.

The process according to the invention produces a methane-rich gas. This methane-rich gas may be used in any application known in the art. For example the methane-rich gas may be used for heating, power supply or chemical processes.

In FIG. 1, one example of a process according to the invention is shown. A synthesis gas stream (102) obtained from a coal gasification process (not shown), comprising carbon monoxide and hydrogen, is desulphurized in a desulphurization unit (104) to produce a desulphurized synthesis gas stream (106). The desulphurized synthesis gas stream (106) is combined with steam provided via a steam stream (108) to provide a water gas shift feed stream (110) that enters a water-gas shift reactor (112). In the water-gas shift reactor, steam and the carbon monoxide react to produce a shifted synthesis gas stream (114), comprising carbon dioxide, hydrogen and unreacted carbon monoxide and unreacted water. The shifted synthesis gas stream (114) is cooled in heat exchanger (115) and used as feed gas stream (116). The feed gas stream (116) is combined with a recycled methane-rich gas stream (117) to produce a gas mixture stream (118) comprising carbon monoxide, carbon dioxide, water, methane and hydrogen. Gas mixture stream (118) is forwarded to a first methanation reactor (120). The first methanation reactor (120) comprises a first catalyst bed (122) comprising a water-gas shift catalyst on top of a second catalyst bed (124) comprising a methanation catalyst.

In the first catalyst bed (122) water and carbon monoxide present in the gas mixture stream (118) are reacted to generate hydrogen and carbon dioxide. As this reaction is exothermic, the temperature of the stream of reactants during this reaction is increased. The stream of increased temperature is subsequently forwarded to the second catalyst bed (124) comprising the methanation catalyst. In the second catalyst bed (124), carbon monoxide and hydrogen are reacted to form methane. The first methanation reactor (120) produces a first stream of methane-rich product gas (126) comprising methane, water, hydrogen, carbon monoxide and carbon dioxide. Stream (126) is cooled in heat exchanger (128) and split into a first split methane-rich gas stream (130) and a second split methane-rich gas stream (132). The first split methane-rich gas stream (130) is cooled down further in a heat exchanger (134), after which a cooled methane-rich gas stream (136) is forwarded to a flash drum (138) to remove water. In the flash drum (138) water is knocked out and discarded via stream (140) and a stream (142) comprising cooled and dried methane-rich gas is produced. Stream (142) is forwarded to a carbon dioxide removal unit (144), where carbon dioxide is removed from the cooled dried methane-rich gas. The carbon dioxide removal unit (144) produces a stream (146) comprising cooled and dried methane-rich carbon dioxide-lean gas. The cooled and dried methane-rich carbon dioxide-lean gas (146) is compressed in compressor (148) and preheated in heat-exchanger (150) to produce a stream of compressed and dried methane-rich carbon dioxide-lean gas (152). This stream of compressed and dried methane-rich carbon dioxide-lean gas (152) can be mixed as recycled methane-rich gas stream (117) with the feed gas stream (116). In addition, optionally part of the stream of compressed and dried methane-rich carbon dioxide-lean gas (152) may be split off as a stream (154), mixed with second split methane-rich gas stream (132) and forwarded to a second methanation reactor (156).

The second split methane-rich gas stream (132) is forwarded to a second methanation reactor (156). The second methanation reactor (156) comprises a first catalyst bed comprising a water-gas shift catalyst (158) on top of a second catalyst bed (160) comprising a methanation catalyst.

The second methanation reactor (156) produces a second stream of methane-rich product gas (162). The second stream of methane-rich product gas (162) is cooled in a heat exchanger (164) and a stream (166) of cooled methane-rich gas is forwarded to a third methanation reactor (168) comprising a catalyst bed with methanation catalyst (170). The third methanation reactor (168) produces a third stream of methane-rich product gas (172). The third stream of methane-rich product gas (172) is cooled in a heat exchanger (174) and a stream (176) of cooled methane-rich gas is forwarded to a flash drum (178) to remove water. In the flash drum (178) water is knocked out and discarded via stream (180) and a stream (182) comprising cooled dried methane-rich gas is produced. Stream (182) is forwarded to a carbon dioxide removal unit (184), where carbon dioxide is removed from the cooled dried methane-rich gas. The carbon dioxide removal unit (184) produces a final product stream (186) comprising cooled dried methane-rich carbon dioxide-lean gas that may be brought to a desired pressure in compressor (188).

The heat recovered in heat exchangers (115), (128), (134), (164) and (174) is used to convert water into steam.

The process according to the invention will hereafter be illustrated by the following non-limiting examples.

Example 1

A computer calculation was made for methane production according to a process as illustrated in FIG. 1 on the basis of a plant producing 14.1 million standard cubic meters of methane-rich product gas per day, with the help of a simulation carried out in Aspen plus 2006.5

In this calculation a water gas shift feed stream comprising a mixture of desulphurized synthesis gas and water is shifted over a high temperature water-gas shift catalyst in a high temperature water-gas shift reactor to produce a shifted synthesis gas stream. The shifted synthesis gas stream is cooled to form a feed gas stream (116) and mixed with recycled methane-rich gas stream (117) to generate a gas mixture stream (118). The particulars of a feed gas stream (116), recycled methane-rich gas stream (117) and gas mixture stream (118) are listed in table I.

TABLE I

Particulars of feed gas stream (116), recycled methane-rich gas stream (117) and gas mixture stream (118).

| composition(mol %) | 116 | 117 | 118 |
|---|---|---|---|
| water | 36.1 | 0.0 | 32.7 |
| nitrogen | 0.2 | 0.9 | 0.2 |
| argon | 0.0 | 0.2 | 0.1 |
| hydrogen | 33.9 | 43.7 | 34.8 |
| carbon monoxide | 5.6 | 9.0 | 5.9 |
| methane | 0.0 | 38.8 | 3.6 |
| carbon dioxide | 24.2 | 7.4 | 22.7 |
| hydrogen sulphide | 0.0 | 0.0 | 0.0 |
| carbonyl sulphide | 0.0 | 0.0 | 0.0 |
| flow (Kmol/sec) | 26.7 | 2.7 | 29.4 |
| Temperature(° C.) | 270.0 | 270.0 | 270.0 |

As illustrated in table I, the process uses a ratio of recycled methane-rich gas to feed gas of 0.10:1 to form the mixture that is being fed into the methanation reactor.

The gas mixture stream (118) is converted over a fixed bed of water-gas shift catalyst and a fixed bed of methanation catalyst in a first methanation reactor into a stream of methane-rich product gas (126).

Stream (126) was cooled and split into a first split methane-rich gas stream and a second split methane-rich gas stream. The first split methane-rich gas stream is recycled as stream (117) after cooling and water and carbon dioxide removal. The second split methane-rich gas stream (132) is forwarded to a second methanation reactor and converted into a second stream of methane-rich product gas (162). The second stream of methane-rich product gas (162) is cooled to a temperature of 300° C., forwarded to a third methanation reactor and converted into a third stream of methane-rich product gas (172).

The particulars of streams (126), (132), (162) and (172) are listed in table II.

TABLE II

Particulars of the first methane-rich product gas stream (126), the second split methane-rich gas stream (132), the second stream of methane-rich product gas (162) and the third stream of methane-rich product gas (172).

| composition (mol %) | 126 | 132 | 162 | 172 |
|---|---|---|---|---|
| water | 49.1 | 49.1 | 56.9 | 58.8 |
| nitrogen | 0.3 | 0.3 | 0.3 | 0.3 |
| argon | 0.1 | 0.1 | 0.1 | 0.1 |
| hydrogen | 13.4 | 13.4 | 3.0 | 0.5 |
| carbon monoxide | 2.8 | 2.8 | 0.2 | 0.0 |
| methane | 11.9 | 11.9 | 16.3 | 17.2 |
| carbon dioxide | 22.5 | 22.5 | 23.4 | 23.2 |
| hydrogen sulphide | 0.0 | 0.0 | 0.0 | 0.0 |
| carbonyl sulphide | 0.0 | 0.0 | 0.0 | 0.0 |
| flow (Kmol/sec) | 25.5 | 16.5 | 15.5 | 15.3 |
| Temperature(° C.) | 630.0 | 270.0 | 439.9 | 299.1 |

As illustrated in table II, the product stream of the first methanation reactor can be split up in a ratio of gas to be recycled and gas to be forwarded to the second methanation reactor of 9:16.5, i.e. a ratio of less than 1:1.

Comparative Example 2

As a comparative example 2a computer calculation was made for methane production according to a conventional process as described in the report titled "Haldor Topsøe's Recycle Energy-efficient methanation process", with the help of a simulation carried out in Aspen plus 2006.5. Comparative example 2 was calculated for the same feed and product. Both example 1 and comparative example 2 were calculated for a system comprising three methanation reactors.

Figure 2:
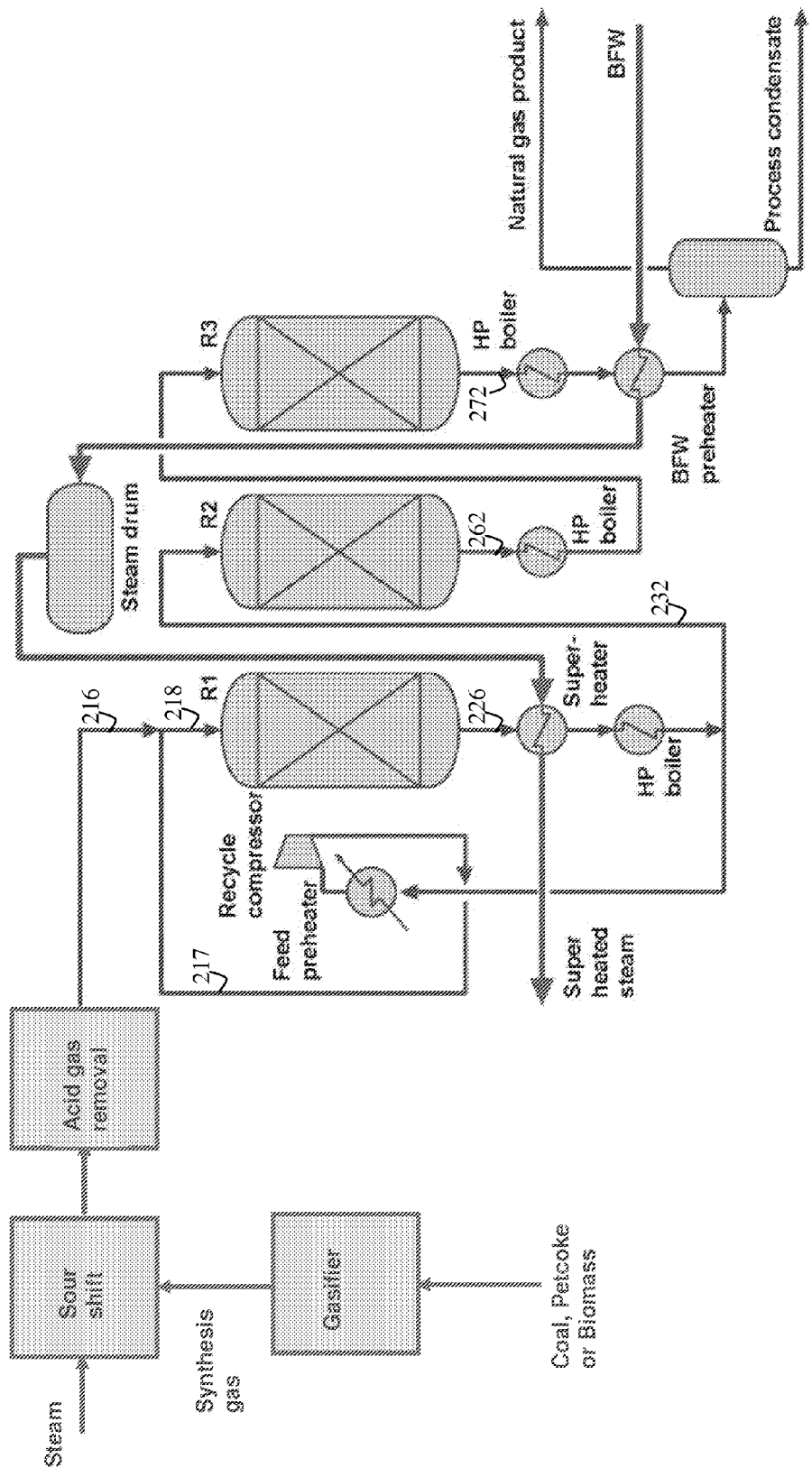
FIG. 2 schematically shows the flow scheme for an example of a conventional methanation process.

The process of comparative example 2 is illustrated in FIG. 2.

In comparative example 2 synthesis gas comprising carbon monoxide and hydrogen is shifted in a sour shift unit to produce a shifted synthesis gas. (By a sour shift unit is here understood a water-gas shift unit carried out on synthesis gas still containing acid gasses such as carbon dioxide and sulphur hydride). After the sour shift, acid gasses such as carbon dioxide and hydrogen sulphide are removed in an acid gas removal unit to prepare a feed gas stream (216). In the calculation it was presumed that in the acid gas removal unit all carbon dioxide was removed from the shifted synthesis gas. The feed gas stream (216) is mixed with a recycled methane-rich gas stream (217) to generate a gas mixture stream (218). The particulars of a feed gas stream (216), recycled methane-rich gas stream (217) and gas mixture stream (218) for comparative example 2 are listed in table III.

The gas mixture stream (218) is converted in a first methanation reactor into a stream of methane-rich product gas (226). Stream (226) was cooled and split into a first split methane-rich gas stream and a second split methane-rich gas stream. The first split methane-rich gas stream is recycled as stream (217). The second split methane-rich gas stream (232) is forwarded to a second methanation reactor and converted into a second stream of methane-rich product gas (262). The second stream of methane-rich product gas (262) is cooled and forwarded to a third methanation reactor and converted into a third stream of methane-rich product gas (272).

The particulars of streams (226), (232), (262) and (272) are listed in table IV.

TABLE III

Particulars of feed gas stream (216), recycled methane-rich gas stream (217) and gas mixture stream (218).

| composition(mol %) | 216 | 217 | 218 |
|---|---|---|---|
| water | 0.0 | 40.0 | 31.6 |
| nitrogen | 0.4 | 0.8 | 0.7 |
| argon | 0.1 | 0.2 | 0.2 |
| hydrogen | 74.6 | 12.7 | 25.7 |

TABLE III-continued

Particulars of feed gas stream (216), recycled methane-rich gas stream (217) and gas mixture stream (218).

| composition(mol %) | 216 | 217 | 218 |
|---|---|---|---|
| carbon monoxide | 24.9 | 0.2 | 5.4 |
| methane | 0.0 | 43.1 | 34.0 |
| carbon dioxide | 0.0 | 3.0 | 2.4 |
| hydrogen sulphide | 0.0 | 0.0 | 0.0 |
| carbonyl sulphide | 0.0 | 0.0 | 0.0 |
| flow (Kmol/sec) | 10.61 | 39.9 | 50.5 |
| Temperature(° C.) | 250 | 280 | 272.0 |

TABLE IV

Particulars of the stream (226), stream (232), stream(262) and stream (272).

| composition (mol %) | 226 | 232 | 262 | 272 |
|---|---|---|---|---|
| water | 40.0 | 40.0 | 46.8 | 48.4 |
| nitrogen | 0.8 | 0.8 | 0.8 | 0.8 |
| argon | 0.2 | 0.2 | 0.2 | 0.2 |
| hydrogen | 12.7 | 12.7 | 3.6 | 1.4 |
| carbon monoxide | 0.2 | 0.2 | 0.0 | 0.0 |
| methane | 43.1 | 43.1 | 47.8 | 48.8 |
| carbon dioxide | 3.0 | 3.0 | 0.9 | 0.4 |
| hydrogen sulphide | 0.0 | 0.0 | 0.0 | 0.0 |
| carbonyl sulphide | 0.0 | 0.0 | 0.0 | 0.0 |
| flow (Kmol/sec) | 45.6 | 5.7 | 5.4 | 5.4 |
| Temperature (° C.) | 530.8 | 270.0 | 371.8 | 291.9 |

As illustrated in table IV, the product stream of the first methanation reactor is split up in a ratio of gas to be recycled and gas to be forwarded to the second methanation reactor of 39.9:5.7, i.e. a ratio of about 7:1.

As illustrated by the above tables the process according to the invention allows the first adiabatic reactor to be sufficiently cooled with a recycle stream of merely 2.7 Kmol/sec whereas the comparative process requires a recycle stream of 39.9 Kmol/sec. Further the molar ratio of recycled methane-rich gas to feed gas for the process according to the invention is about 0.1:1, whereas the molar ratio of recycled methane-rich gas to feed gas in the comparative process is about 3.8:1.

As a consequence the flowrate through the first adiabatic reactor for the process according to the invention, i.e. 29.5 Kmol/sec, is much smaller than the flowrate through the first adiabatic reactor for the comparative process, i.e. 50.5 Kmol/sec. It is especially advantageous to reduce the volume of the first adiabatic reactor, because the first adiabatic reactor requires expensive metal to withstand the higher temperatures in the reactor.

What is claimed is:

1. A process for producing a methane-rich gas comprising the steps of:
    a) mixing a feed gas, comprising carbon monoxide and hydrogen, and a recycled methane-rich gas, comprising methane, to produce a gas mixture, comprising carbon monoxide, hydrogen and methane;
    b) reacting at least part of the carbon monoxide and hydrogen in the gas mixture in the presence of a methanation catalyst to produce a methane-rich product gas comprising methane, carbon dioxide and water;
    c) treating at least part of the methane-rich product gas to remove carbon dioxide to produce a methane-rich carbon dioxide-lean gas; and
    d) recycling at least part of the methane-rich carbon dioxide-lean gas to mixing step a) as recycled methane-rich gas;
    wherein in the range from 1 to 99 volume percent of the methane-rich product gas produced in step b) is treated to remove carbon dioxide to produce a methane-rich carbon dioxide-lean gas and wherein essentially all of the methane-rich carbon dioxide-lean gas is recycled to mixing step a) as recycled methane-rich gas.

2. The process according to claim 1, wherein the feed gas in step a) has been desulphurized before mixing the feed gas and the recycled methane-rich gas.

3. The process according to claim 1, wherein step a) further comprises shifting the gas mixture with water and/or steam in a water-gas shift reaction before reacting carbon monoxide and hydrogen in step b).

4. The process according to claim 3, wherein the water-gas shift reaction and the reaction of carbon monoxide and hydrogen are carried out in one reactor vessel.

5. The process according to claim 1, wherein step c) comprises cooling the methane-rich product gas produced in step b) to produce a cooled methane-rich product gas and treating the cooled methane-rich product gas to remove carbon dioxide to produce the methane-rich carbon dioxide-lean gas.

6. The process according to claim 1, wherein step c) comprises cooling the methane-rich product gas produced in step b) to produce a cooled methane-rich product gas; removing water from the cooled methane-rich product gas to produce a dried and cooled methane-rich product gas; and treating the dried and cooled methane-rich product gas to remove carbon dioxide to produce the methane-rich carbon dioxide-lean gas.

7. The process according to claim 1, wherein the molar ratio of recycled methane-rich gas to feed gas in the gas mixture of step a) is equal to or less than 2:1.

8. The process according to claim 1, wherein the recycled methane-rich gas comprises less than 10 volume percent water, less than 10 volume percent carbon dioxide and more than 25 volume percent methane.

9. The process according to claim 1, wherein at least part of the methane-rich product gas produced in step b) and/or at least part of the methane-rich carbon dioxide-lean gas produced in step c) is forwarded to a subsequent adiabatic methanation reactor to produce a further methane-rich product gas.

10. The process according to claim 1, further comprising the use of the methane-rich product gas as a substitute for natural gas.

11. The process according to claim 1, wherein the feed gas in step a) is synthesis gas obtained by reacting a carbonaceous feed and an oxidant in a gasification reaction.

12. The process according to claim 11, wherein step a) comprises
    reacting a carbonaceous feed and an oxidant in a gasification process to produce a synthesis gas comprising carbon monoxide and hydrogen;
    which synthesis gas is desulphurized to produce a desulphurized synthesis gas; and of which desulphurized synthesis gas at least part is reacted with water and/or steam in a water-gas shift reaction to produce a shifted synthesis gas;
    which shifted synthesis gas is mixed with a recycled methane-rich gas, comprising methane, to produce a gas mixture, which gas mixture comprises carbon monoxide, hydrogen and methane.

13. The process according to claim 12, wherein the carbonaceous feed is coal or petroleum coke.

* * * * *